United States Patent
Kostrzewski

(10) Patent No.: US 9,186,134 B2
(45) Date of Patent: *Nov. 17, 2015

(54) SUTURE AND RETAINER ASSEMBLY AND SULU

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/864,570

(22) Filed: Apr. 17, 2013

(65) Prior Publication Data

US 2013/0245645 A1    Sep. 19, 2013

Related U.S. Application Data

(63) Continuation of application No. 13/658,257, filed on Oct. 23, 2012, now Pat. No. 8,435,254, which is a continuation of application No. 12/689,441, filed on Jan. 19, 2010, now Pat. No. 8,313,509.

(51) Int. Cl.
*A61B 17/04* (2006.01)
*A61B 17/06* (2006.01)

(52) U.S. Cl.
CPC ......... *A61B 17/0491* (2013.01); *A61B 17/0401* (2013.01); *A61B 17/0469* (2013.01); *A61B 17/0487* (2013.01); *A61B 17/06066* (2013.01); *A61B 2017/0404* (2013.01); *A61B 2017/0462* (2013.01); *A61B 2017/0464* (2013.01);
(Continued)

(58) Field of Classification Search
CPC ........... A61B 17/0491; A61B 17/0401; A61B 17/0469; A61B 17/0487; A61B 17/06066; A61B 2017/0404; A61B 2017/0462; A61B 2017/0464; A61B 2017/0472; A61B 2017/06042
USPC .......................................... 606/232, 219, 220
See application file for complete search history.

(56) References Cited

U.S. PATENT DOCUMENTS

| | | | |
|---|---|---|---|
| 3,842,840 | A | 10/1974 | Schweizer |
| 5,156,315 | A | 10/1992 | Green et al. |

(Continued)

FOREIGN PATENT DOCUMENTS

| | | |
|---|---|---|
| EP | 0169044 | 1/1986 |
| GB | 2337934 | 12/1999 |

OTHER PUBLICATIONS

European Search Report for EP 11250054.1-1269 date of completion is Jun. 17, 2011 (4 pages).

(Continued)

*Primary Examiner* — Jonathan W Miles
*Assistant Examiner* — Todd J Scherbel

(57) ABSTRACT

A suturing system for receiving and retaining a suture is disclosed and includes a suture, at least one retainer, and at least one needle. Each needle is able to receive and removably retain the suture within a groove located in a tapered end. The retainer has a body that defines an aperture therethrough. The shape of the aperture is formed by a central passageway, and a pair of diametrically opposed slots extending radially outward from the central passageway. The central passageway is sized to allow passage of the needle therethrough. Each slot defines a tortured path section that permits passage of the suture in a first direction and inhibits passage of the suture in a second direction.

16 Claims, 8 Drawing Sheets

(52) U.S. Cl.
CPC .................. *A61B2017/0472* (2013.01); *A61B 2017/06042* (2013.01)

(56) References Cited

U.S. PATENT DOCUMENTS

| | | | |
|---|---|---|---|
| 5,282,832 A | 2/1994 | Toso et al. | |
| 5,630,824 A | 5/1997 | Hart | |
| 5,645,553 A | 7/1997 | Kolesa et al. | |
| 5,725,556 A | 3/1998 | Moser et al. | |
| 5,735,877 A | 4/1998 | Pagedas | |
| 5,843,126 A * | 12/1998 | Jameel | 606/220 |
| 5,895,393 A | 4/1999 | Pagedas | |
| 6,015,428 A | 1/2000 | Pagedas | |
| 6,066,160 A | 5/2000 | Colvin et al. | |
| 6,086,608 A | 7/2000 | Ek et al. | |
| 6,533,795 B1 * | 3/2003 | Tran et al. | 606/144 |
| 7,094,251 B2 | 8/2006 | Bonutti et al. | |
| 7,166,116 B2 | 1/2007 | Lizardi et al. | |
| 7,625,387 B2 | 12/2009 | Wixey et al. | |
| 7,879,046 B2 | 2/2011 | Weinert et al. | |
| 8,313,509 B2 * | 11/2012 | Kostrzewski | 606/232 |
| 8,435,254 B2 * | 5/2013 | Kostrzewski | 606/144 |
| 2002/0147456 A1 | 10/2002 | Diduch et al. | |
| 2003/0065336 A1 | 4/2003 | Xiao | |
| 2003/0233106 A1 | 12/2003 | Dreyfuss | |
| 2004/0133238 A1 | 7/2004 | Cerier | |
| 2006/0229671 A1 | 10/2006 | Steiner et al. | |
| 2007/0010832 A1 | 1/2007 | Manzo | |
| 2007/0250118 A1 | 10/2007 | Masini | |
| 2007/0270885 A1 | 11/2007 | Weinert et al. | |
| 2009/0281563 A1 | 11/2009 | Newell et al. | |
| 2011/0118760 A1 | 5/2011 | Gregoire et al. | |
| 2011/0238090 A1 * | 9/2011 | Heneveld | 606/144 |

OTHER PUBLICATIONS

European Search Report dated Aug. 3, 2015, cited in European Application No. 15175739.

* cited by examiner

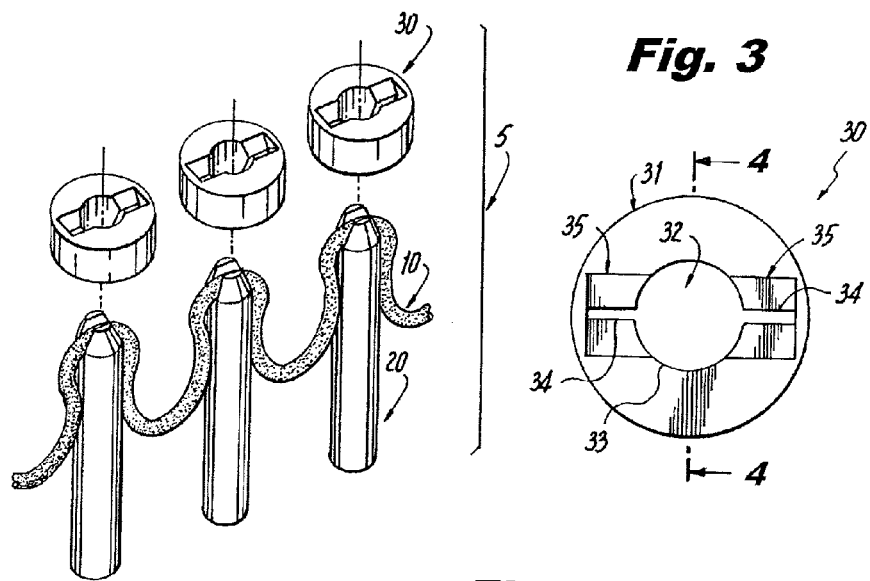
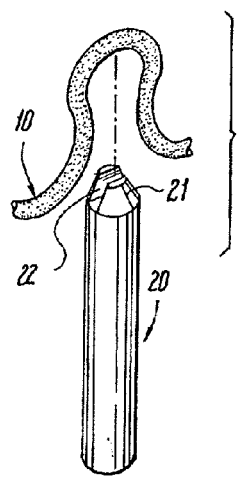
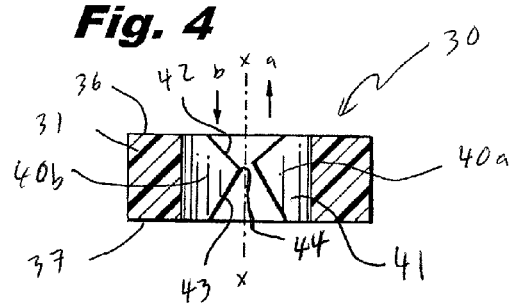
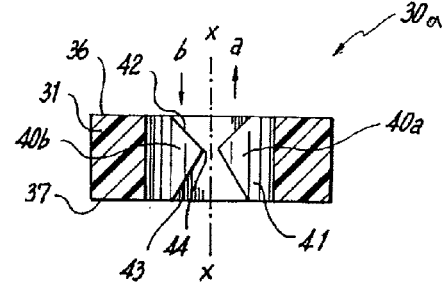
Fig. 1
Fig. 2
Fig. 3
Fig. 4
Fig. 4a

Fig. 7
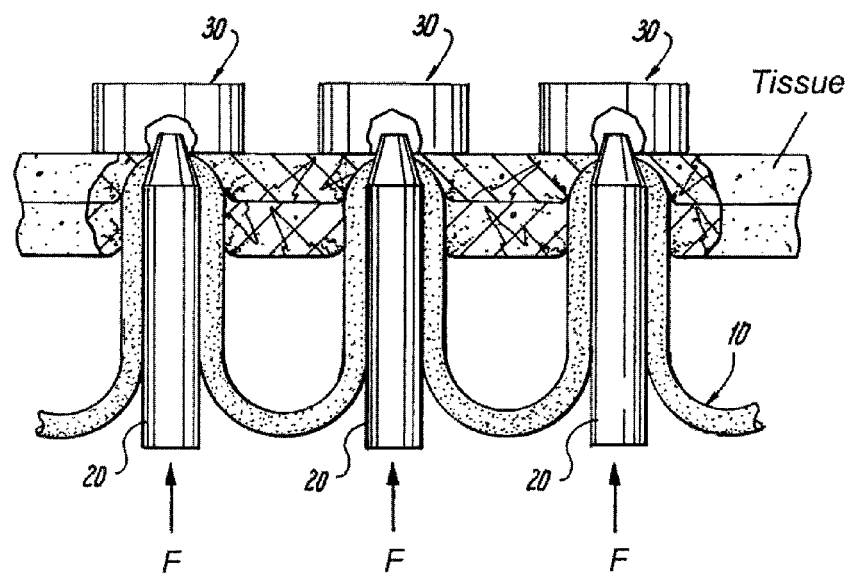
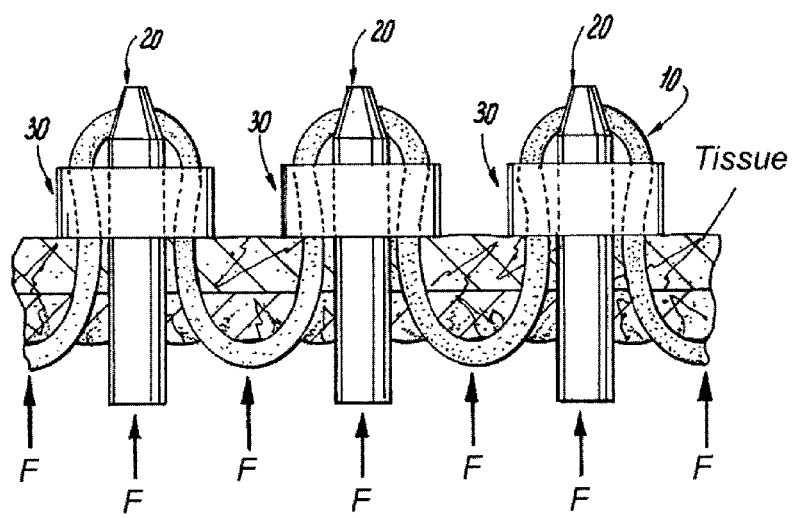
Fig. 8

SUTURE AND RETAINER ASSEMBLY AND SULU

This application is a continuation of U.S. patent application Ser. No. 13/658,257, which was filed on Oct. 23, 2012, now U.S. Pat. No. 8,435,254, which is a continuation of U.S. patent application Ser. No. 12/689,441, which was filed Jan. 19, 2010, now U.S. Pat. No. 8,313,509. The entire contents of each of the above applications are hereby incorporated herein by reference.

BACKGROUND

1. Technical Field

This application relates to a surgical suturing device. More particularly, the present disclosure relates to a suturing system, an instrument for applying the suturing system, and a method for applying the suturing system using the instrument.

2. Related Art

Surgical fastener-applying devices are well known, wherein opposing jaw structures grasp and clamp selected tissue, which is then joined by means of surgical fasteners. Typically, one of the jaw members includes a cartridge which houses a plurality of staples arranged in two or more linear rows and the other jaw member includes an anvil having a plurality of staple forming pockets for receiving and forming the legs of the staples. Linear stapling instruments, for example, include two elongated jaw members, movable relative to each other, to capture or clamp tissue.

Surgical fastener-applying devices utilizing two-part fasteners are also known. Two-part fasteners include a barbed fastener used in conjunction with a retaining piece to hold the fastener in place. Typically, the two-part fastener comprises a back-span and two barbed prongs which are engaged and locked into a separate retainer piece. In use, the fastener is pressed into the body tissue so that the barbs penetrate the tissue and emerge from the other side where they are then locked into the retainer piece. The retainers prevent the fastener from working loose from the tissue. The two piece fasteners cannot be unlocked and are not easily removable. For this reason, they are typically made of a bioabsorbable material.

SUMMARY

The present disclosure pertains to a suturing system for receiving and retaining a suture including a quantity or portion of suture, at least one needle, and at least one retainer. Each needle has the ability to receive and removably retain the suture. Both the suture and the retainer may be made from a biocompatible material that is absorbable by a patient's body. Each retainer includes a body that defines an aperture therethrough.

The shape of the aperture is formed by a central passageway, which defines a longitudinal axis, and a pair of diametrically opposed slots extending radially outward from the central passageway. The central passageway and diametrically opposed slots form a O-shaped cross-sectional hole within the body, defined by a substantially circular center and two opposed rectangles extending radially outward from the substantially circular center. The central passageway is sized to allow passage of the needle therethrough.

The diametrically opposed slots extend the longitudinal length of the body and define a tortured path section. The tortured path section permits passage of the suture in a first direction and inhibits passage of the suture in a second direction. The tortured path is defined by at least one protrusion extending from a sidewall of the slot. The at least one protrusion has a distal surface, a proximal surface, and an apex. The distal surface of the protrusion has a larger area than that of the proximal surface of the protrusion.

As discussed herein, the tortured path section has two protrusions with the apices being offset from each other, such that one apex is longitudinally higher than another apex. It is also envisioned that the apices be adjacent each other and in immediate proximity. The tortured path section can also contain either a single protrusion or more than two protrusions.

As discussed herein, the suture is a conventional cylindrical shape, however it is envisioned that the suture includes a series of tapered sections configured to aid in the retention of the suture within the tortured path section of the suture retainer.

The outer perimeter of the body is generally in the shape of an oval, a circle, a triangle, or a rectangle. It is also envisioned that the body has an outer perimeter that links one or more of these shapes together.

It is also envisioned that the central passageway has a substantially conical shape.

Also disclosed herein is a surgical suturing instrument including a handle assembly, an elongate member, an end effector, and an actuation mechanism for applying the suturing system in a patient's tissue. The actuation mechanism is located within the handle assembly and is operatively connected to the end effector through the elongate member. The elongate member extends distally from the handle assembly and defines a longitudinal axis, a proximal end, and a distal end. The end effector is attached to the distal end of the elongate member. The end effector has a first jaw or suture jaw and a second jaw or retainer jaw. The suture jaw has a suture cartridge with at least one removably secured suture and the retainer jaw has a retainer cartridge with at least one removably secured retainer. Both the suture cartridge and retainer cartridge are replaceable and are removably secured within the respective jaws.

The suture cartridge includes a body and a series of needles. Each needle extends from the body and has a tapered proximal end and a groove or slot, across the tapered proximal end, for receiving and removably retaining the suture therein. The series of needles is arranged such that the groove in each needle is in alignment with the groove of at least one other needle located in an adjacent position.

The retainer cartridge includes a body with a series of holes. The retainers are arranged about the holes to allow one of the needles to pass through the retainer and into the hole.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

FIG. 1 is a perspective view of a suturing system in accordance with the principles of the present disclosure, illustrating a suture, a plurality of needles, and a plurality of retainers;

FIG. 2 is a perspective view of the needle and suture;

FIG. 3 is a top plan view of the retainer of FIG. 1;

FIG. 4 is a side cross-sectional view of the retainer of FIG. 1 taken along section line 4-4 of FIG. 3, wherein the apices are offset from each other;

FIG. 4a is a side cross-sectional view of another embodiment of the retainer of FIG. 4, wherein the apices are adjacent to each other;

FIG. 7 is a side view of the suturing system with needles and suture entering retainers;

FIG. 8 is a side view of the suturing system with needles and suture inserted into retainers;

Figure 5:
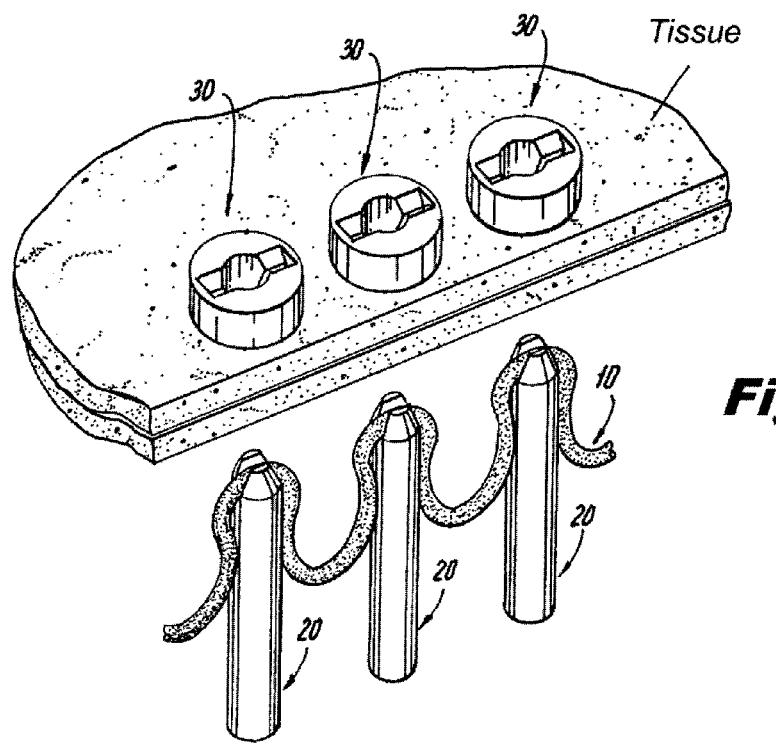
FIG. 5 is a perspective view of the suturing system and tissue.
Figure 6:
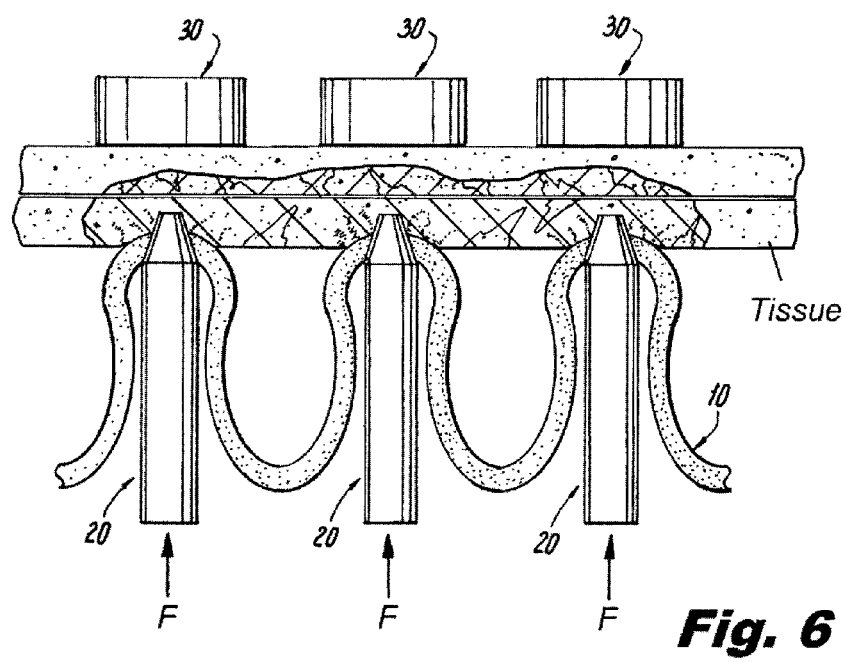
FIG. 6 is a side view of the suturing system through tissue with needles and suture entering the tissue.
Figure 9:
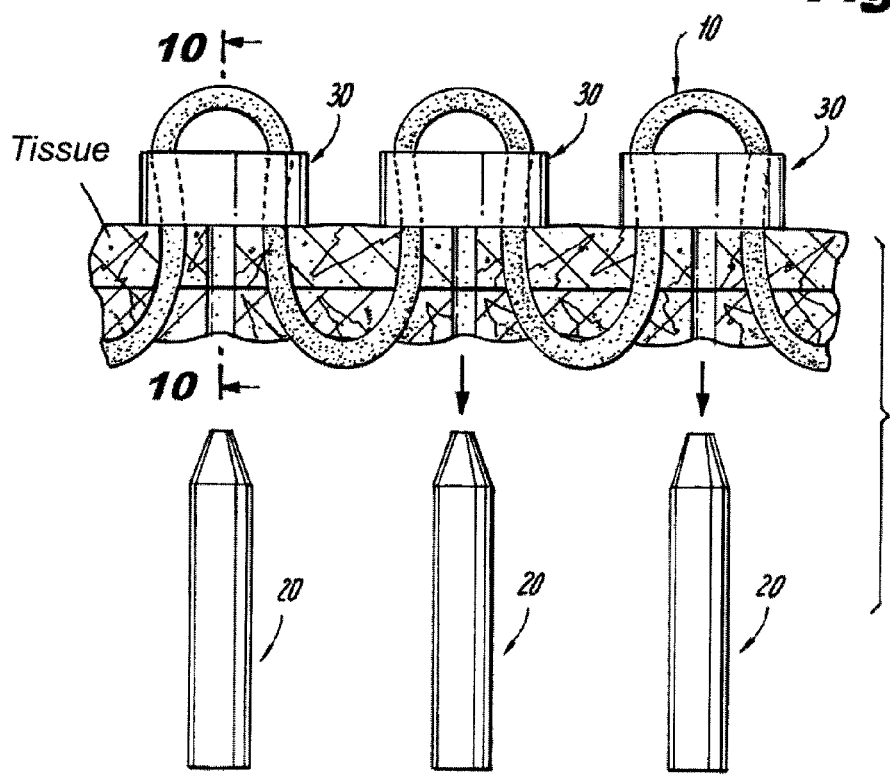
FIG. 9 is a side view of the suturing system with needles retracted.
Figure 10:
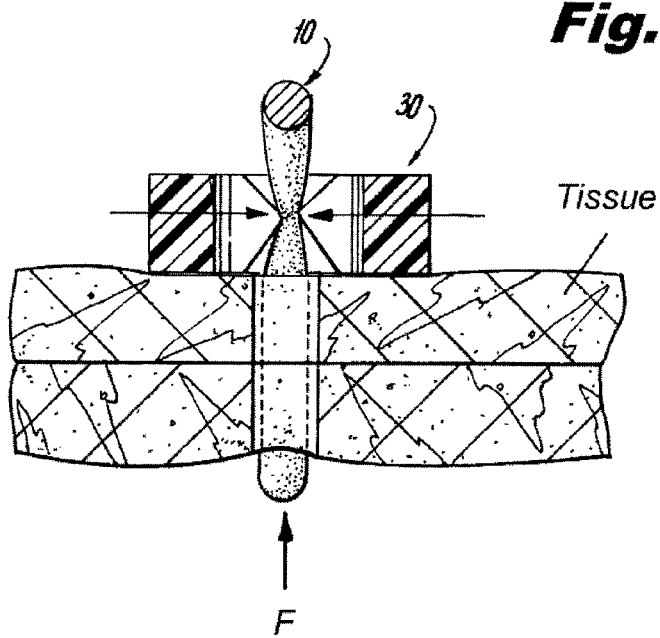
FIG. 10 is a side cross-sectional view of the suture disposed within the retainer.

Other features of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed suturing system and surgical suturing instrument are described in detail with reference to the drawings, in which like reference numerals designate identical or corresponding elements in each of the several views. As used herein, the term "distal" refers to that portion of the surgical suturing instrument, or component thereof, farther from the user while the term "proximal" refers to that portion of the surgical suturing instrument or component thereof, closer to the user.

The suturing system and surgical suturing instrument with which the disposable loading unit of the present disclosure is discussed shall be discussed in terms of both conventional and endoscopic procedures. It is contemplated that the suturing system and surgical suturing instrument described herein may find use in procedures wherein access is limited to a small incision including but not limited to arthroscopic and/or laparoscopic procedures, and in other non-endoscopic (e.g. open) procedures.

Referring now to the drawings, wherein like reference numerals identify similar structural elements of the subject system and instrument, there is illustrated in FIG. 1 a suturing system, designated generally by reference numeral 5. Suturing system 5 includes a quantity of suture 10, at least one needle 20, and at least one retainer 30. Both the portion of suture 10 and the retainer 30 are made of a biocompatible material. The biocompatible material may be absorbable in a patient's body.

Now referring to FIG. 2, each of the needles 20 has a tapered proximal end 21 and a groove 22, across the tapered proximal end 21, for receiving and removably retaining the portion of the suture 10 therein. The needles 20 are arranged such that the groove 22 in each needle 20 is in alignment with the groove 22 of at least one other needle 20 that is located in an adjacent position.

Now referring to FIGS. 3 and 4, the retainer 30 includes a body 31 that defines an aperture 32 therethrough. The shape of the aperture 32 is defined by a central passageway 33, which defines a longitudinal axis 'x' and a pair of diametrically opposed slots 34 extending radially outward from the central passageway 33. The aperture 32 forms a cross-sectional Φ-shaped hole in the body 31 defined by a substantially circular center and two opposed rectangles extending radially outward therefrom. The central passageway 33 has a substantially constant cylindrical shape sized to allow passage of the needle 20 therethrough.

A tortured path section 35 is defined by two protrusions 40a, 40b that extend from slots 34. Each protrusion 40a, 40b extends from one of the sidewalls of the slots 34. Each of the two protrusions 40a, 40b has a proximal surface 42, a distal surface 43, and an apex 44. The proximal surface 42 forms an angle with respect to the longitudinal axis 'x' that is greater than an angle formed by the distal surface 43 intersecting with the longitudinal axis 'x'. As a result, the area of the distal surface 43 is larger than the area of the proximal surface 42. The tortured path section 35 permits passage of the portion of suture 10 in a first direction 'a' and inhibits passage of the portion of suture 10 in a second direction 'b'.

The outer perimeter of the body 31 is disclosed as being generally circular in the shape, however this should not be taken to be a limitation. The body can also be in a generally oval, rectangular, or triangular shape. It is also envisioned that the body have an outer perimeter that links one or more of these shapes together and that more than one suture can be retained within a single body.

As discussed herein and illustrated in FIG. 4, the tortured path section 35 has two protrusions 40a, 40b with offset apices 44, such that one apex is longitudinally higher than another apex. It is also envisioned that the apices are adjacent to each other, as shown in another embodiment of retainer in FIG. 4a. The adjacent apices 44 are in immediate proximity. The tortured path section 35 can also contain either a single protrusion or more than two protrusions.

As discussed herein, the portion of suture 10 is a conventional cylindrical shape, however it is envisioned that the portion of suture 10 includes a series of tapered sections configured to aid in the retention of the portion of suture 10 within the tortured path section 35 of the suture retainer 30.

It is also envisioned that the central passageway 33 has a substantially conical shape.

Now referring to FIGS. 5-10, in use the retainers 30 are positioned on one side of the tissue and the needles 20 are positioned on the other side of the tissue. The needles 20 are aligned with the longitudinal axis 'x' of the retainers 30. As a force F is applied to the needles 20, the needles 20 and the portion of suture 10 are forced to penetrate through the tissue, causing the needles 20 to extend into the central passageway 32 of the retainers 30.

The continued application of force F moves the tapered proximal end 21 of the needle 20 with the groove 22 beyond the retainer 30. As a result, the portion of suture 10 is forced into and through the tortured path sections 35 of the retainers 30. The close proximity of the apices 44 pinch or squeeze the portion of suture 10 to retain it in position within the retainers 30 and allow the needles 20 to be removed.

Figure 11:
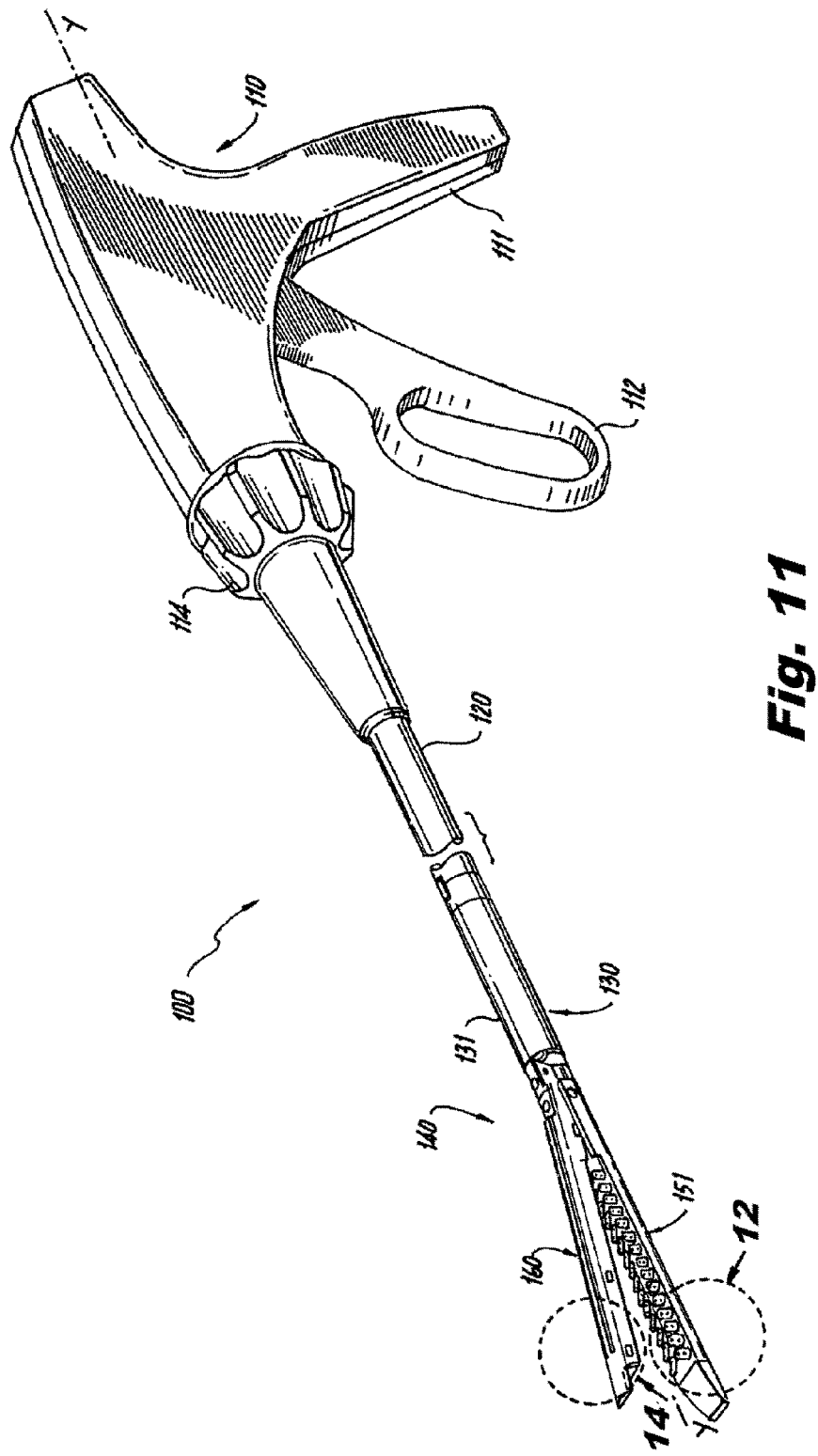
FIG. 11 is a perspective view of a surgical apparatus in accordance with the principles of the another embodiment of the present disclosure.

Also disclosed is a surgical suturing instrument 100, shown in FIG. 11. Various embodiments of the present disclosure are described hereinbelow with reference to the accompanying drawings. Well-known functions or constructions are not described in detail to avoid obscuring the present disclosure in unnecessary detail. Those skilled in the art will understand that the present disclosure may be adapted for use with either an endoscopic instrument or an open instrument.

The surgical suturing instrument includes the loading unit, e.g., a single use loading unit ("SULU") or disposable loading unit ("DLU") into tissue of a patient and the method of use of the instrument. For simplicity, hereinafter, SULU and DLU will be referred to as "SULU", but it should be understood to include either or both a DLU or SULU.

Suture 210, needle 220, and retainer 230 are substantially similar to suture 10, needle 20, and retainer 30, respectively, and will only be described as relates to the differences therebetween.

Many components of the surgical suturing instrument 100 are substantially as described in U.S. Pat. No. 6,032,849, which is incorporated herein in its entirety by reference. It is contemplated that the presently disclosed embodiments of the end effector 140 may be used in association with other known stapling devices of both endoscopic and open construction. These devices include articulating and non-articulating devices, as well as, reusable and non-reusable devices.

The surgical suturing instrument 100 includes a handle assembly 110, an elongate member 120, and an end effector 140. The handle assembly 110 includes a stationary grip member 111, a pivotable trigger 112, and a rotation knob 113. An actuation mechanism 114 is located within the handle assembly 110 and is operatively connected to the pivotable trigger 112. The actuation mechanism 114 extends through the elongate member 120 and operatively connects with the end effector 140. The pivotable trigger 112 is actuated through an actuation stroke or strokes to advance the actuation mechanism 114 within the end effector 140.

The elongate member 120 extends distally from the handle assembly 110 and defines a longitudinal axis 'y', a proximal end 121, and a distal end 122. A tool 130 (e.g., SULU) is attached to the distal end 122 of the elongate member 120. The TOOL 130 is adapted to be releasably attached to the elongate member 120 and includes a proximal body portion 131 and the end effector 140. The end effector 140 includes a retainer jaw 150 and a suture jaw 160, which are respectively used to capture and clamp tissue therebetween. The suture jaw 160 and the retainer jaw 150 are pivotable in relation to each other between an open position and a clamped or approximated position.

Advancement of the actuation mechanism 114 moves the suture jaw 160 in relation to the retainer jaw 150 between an open position and a clamped position and to eject sutures 210 from the suture cartridge 161. Alternatively, the actuation stroke may pivot the retainer jaw 150 towards a stationary suture jaw 160.

Now referring to FIGS. 12-15, the suture jaw 160 includes a suture cartridge 161 containing at least one removably secured suture 210 and the retainer jaw 150 includes a complementary retainer cartridge 151 containing at least one removably secured retainer 230. Both the suture cartridge 161 and retainer cartridge 151 are replaceable and are removably secured within the respective jaws. It is contemplated that both the suture cartridge 161 and retainer cartridge 151 contain one or more complementary rows of sutures 210 and retainers 230, respectively.

Figure 14:
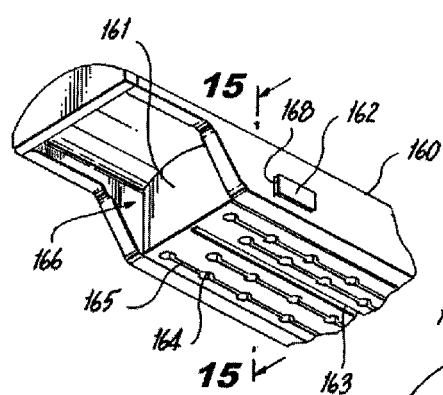
FIG. 14 is a perspective view of a portion of a suture jaw and suture cartridge of the surgical apparatus of FIG. 11.
Figure 15:
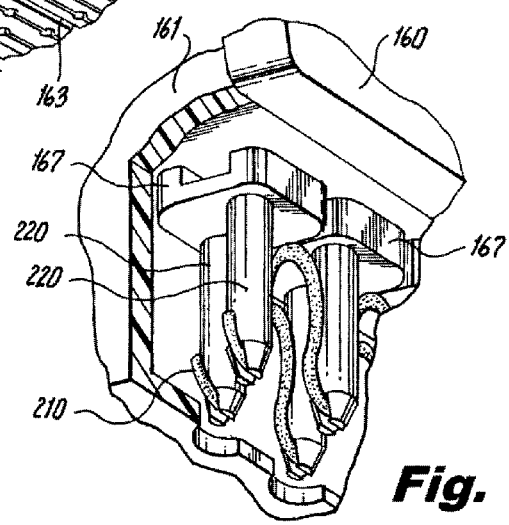
FIG. 15 is a cut away view of the suture jaw and suture cartridge illustrating storage position of needles and suture.

Now referring to FIGS. 14-15, the end effector 140 is illustrated in accordance with an embodiment of the present disclosure. The suture cartridge 161 is located within a suture cartridge channel 166 of the suture jaw 160. The suture cartridge channel 166 is dimensioned and configured to receive the suture cartridge 161 therein. The suture cartridge 161 includes tabs 162 formed along either side of the suture cartridge 161 dimensioned and configured to secure to a corresponding tab recess 168 formed along either side of the suture cartridge channel 166. The tab recess 168 is configured to retain, position, and align the tabs 162 of the suture cartridge 161 therein. Any other conventional method may also be used to secure the suture cartridge 161 within the suture cartridge channel 166.

Figure 17:
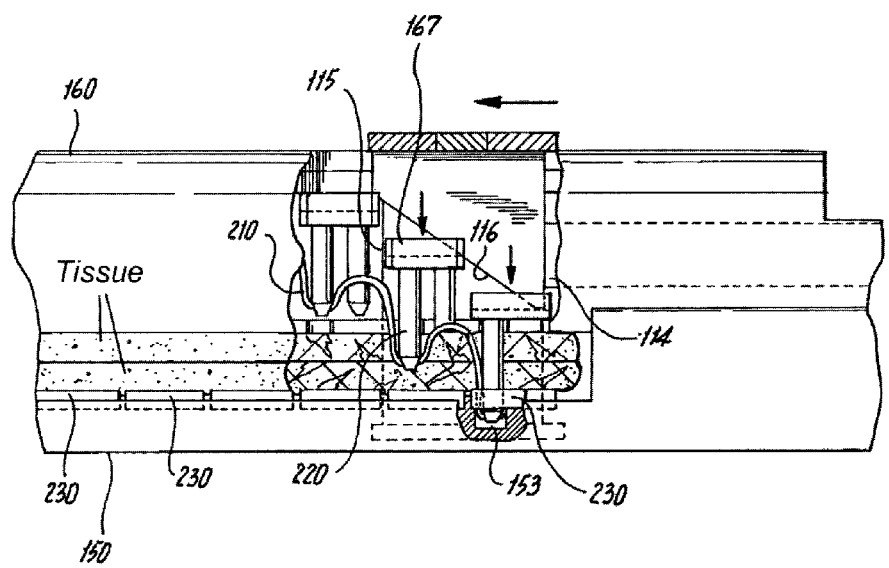
FIG. 17 is a side partial cut away view of the end effector of FIG. 16 as cam advances through end effector.
Figure 18:
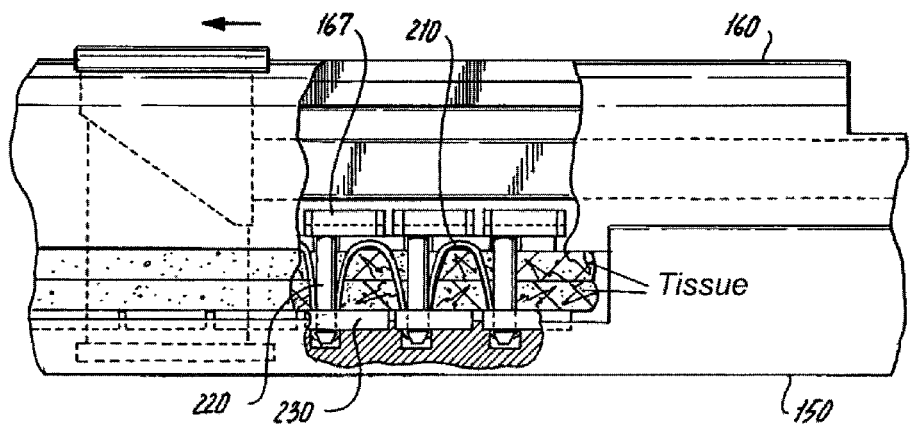
FIG. 18 is a side partial cut away view of the end effector of FIG. 16 showing further advancement of the cam.

The suture cartridge 161 contains a plurality of linear rows of needles 220 and complementary needle openings 164. Each needle opening 164 is linked to another needle opening 164 by a suture passage 165. A knife slot 163 separate at least two linear rows of needles 220 and allows passage of a knife 115 therethrough, as seen in FIG. 17. A longitudinal slot 169 may extend longitudinally along the top of the suture cartridge channel 166 to provide an additional point of fixation and visual indication of the position of the knife 115 with respect to the suture cartridge channel 166.

Each row of needles 220 is parallel to the longitudinal axis 'y', within the suture cartridge 161, while each individual needle 220 is perpendicular with respect to the longitudinal axis 'y'. Each row of needles 220 is arranged such that the groove in each needle 220 is in alignment with the groove of at least one other needle 220 that is located in an adjacent position. Each needle 220 is connected to a needle base 167. Multiple needles 220 may be connected to a single needle base 167.

The suture cartridge 161 contains a cam member 116 for acting upon the needle base 167 to sequentially move the needles 220 perpendicular to the longitudinal axis 'y' to extend the needles 220 from the suture cartridge 161. As the needles 220 are extended out of the suture cartridge 161, the needles 220 and suture 210 are forced through the tissue and into the retainer.

Figure 12:
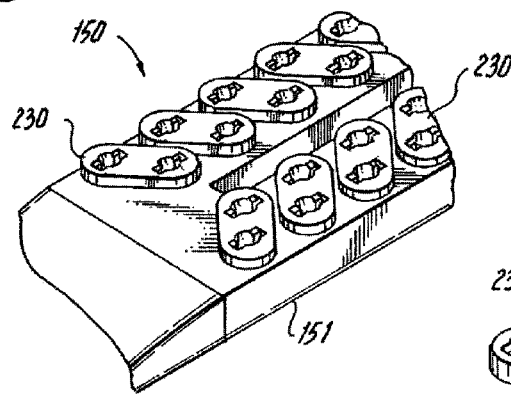
FIG. 12 is a perspective view of a retainer jaw and retainer cartridge of the surgical apparatus of FIG. 11.
Figure 13:
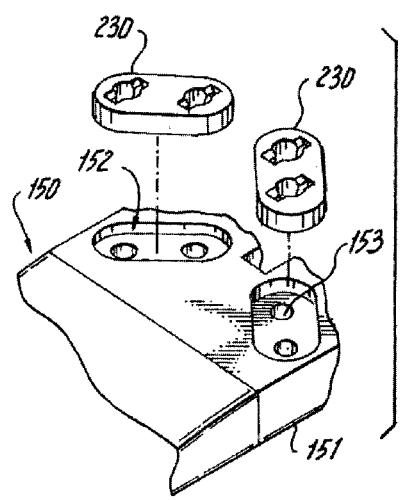
FIG. 13 is a perspective view of a portion of the retainer jaw with retainers separated from the retainer cartridge.

Now referring to FIGS. 12-13, the retainer cartridge 151 includes a series of retainers 230 releasably secured within a series of retainer recesses 152, and a series of holes 153 aligned with the apertures of the retainers 230. The series of holes 153 complement the rows of needles 220 in the suture cartridge 161. The retainers 230 have two apertures and are aligned with the holes 153 to allow at least one of the needles 220 and the portion of the suture 210 to pass through the retainer 230 and into the hole 153. The sutures 210 are set in the needles 220 with slack in between the needles 220 to accommodate various thicknesses of tissue.

It is also envisioned that the needles 220 and retainers 230 are aligned along curved jaws.

Figure 16:
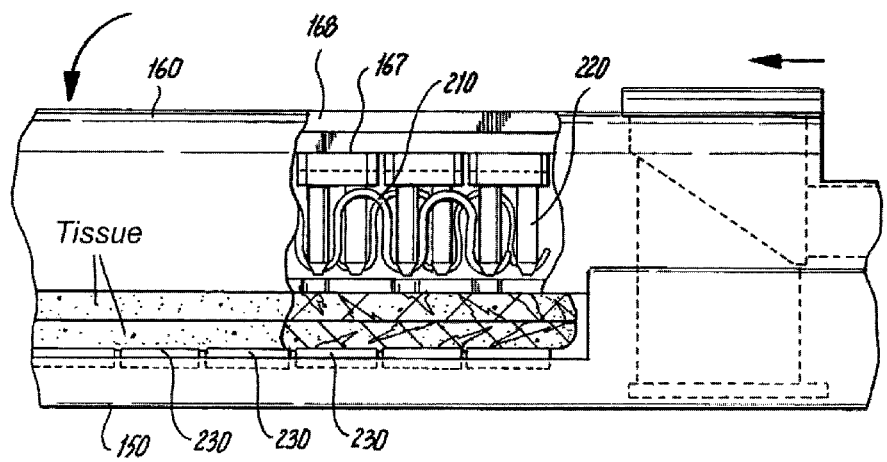
FIG. 16 is a side partial cut away view of a portion of the end effector with tissue disposed between the jaws.
Figure 19:
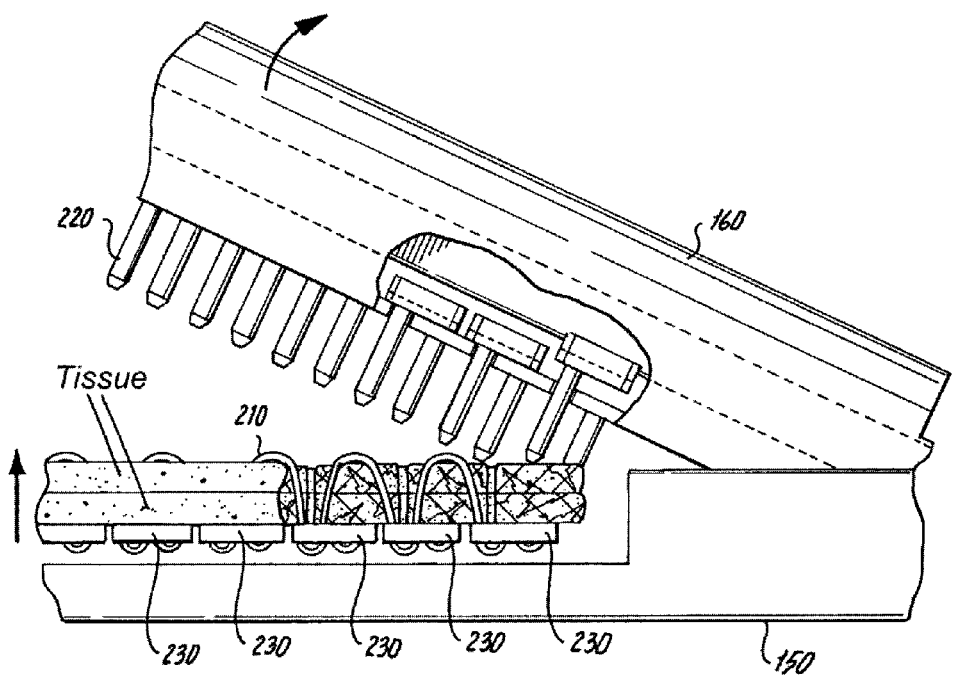
FIG. 19 is a side partial cut away view of the end effector of FIG. 16 showing sutures set within retainers and unapproximated jaws.

Now referring to FIGS. 16 and 19, the present disclosure also relates to a surgical method for utilizing the surgical suturing instrument 100.

During dissection of tissue, the end effector 140 is adapted to access a surgical site through an access device that is known in the art. To accomplish this, the end effector 140 including the retainer jaw 150 and the suture 160 is maintained in a clamped or approximated position as the elongate member 120 is inserted through a cannula (not shown).

Thereafter, the jaws 150, 160 can be opened and tissue can be joined and/or cut by clamping and actuating the surgical suturing instrument 100.

As shown in FIG. 16, tissue is place between the retainer jaw 150 and the suture jaw 160. As the pivotable trigger 112 is actuated, the actuation mechanism 114 is driven distally along the suture jaw 160, illustrated in FIG. 17, while pushing the cam 116 and the knife 115 to cut the tissue. As the cam 116 advances, along the longitudinal axis 'y', the cam 116 acts upon the needle base 167 to move the needles 220 and sutures 210 perpendicularly from the suture cartridge 161. The needles 220 and the portion of suture 210 extend through the tissue and into the retainers 230, and partially through the retainers 230.

Upon completion of the advancement of the cam 116 across the needle bases 167, the actuation mechanism 114 is retracted distally. As the actuation mechanism 114 is retracted, the cam 116 and knife 115 are also retracted distally allowing the needles 220 to retract perpendicularly into the suture cartridge 161. As the needles 220 are retracted, the sutures 210 are released from the needles 220 and locked into place within the retainers 230.

The retainers 230 are separated from the retainer cartridge 161 as the end effector 140 releases the tissue. After the actuation mechanism 114 is fully retracted, the surgical suturing instrument 100 can be removed from the surgical site. Adjusting the width of the gap between the retainer jaw 150 and suture jaw 160 allows the use of the surgical suturing instrument 100 with a variety of tissue thicknesses.

It will be understood that various modifications may be made to the embodiments disclosed herein. For example, the size, angles and/or curves of the cartridge assembly's surface(s) may be modified to better suit a particular surgical procedure. Therefore, the above description should not be construed as limiting, but merely as exemplifications of various embodiments. Those skilled in the art will envision other modifications within the scope and spirit of the claims appended hereto.

What is claimed is:

1. A method of applying a surgical fastener, comprising:
   clamping tissue between a needle cartridge having needles and a retainer cartridge having retainers;
   driving each of the needles out of the needle cartridge and into a respective retainer of the retainers, each needle drawing a length of a suture in a first direction through the clamped tissue and through a tortured path section defined by the respective retainer, the tortured path section inhibiting the length of the suture disposed within the tortured path section from moving in a second direction opposite the first direction; and
   separating the needle cartridge from the retainer cartridge to withdraw the needles from the retainers and to separate the retainers from the retainer cartridge.

2. The method according to claim 1, further comprising securing the needle cartridge to a surgical instrument, wherein the needle cartridge is removably secured to an end effector of the surgical instrument.

3. The method according to claim 1, wherein driving each of the needles draws the length of the suture from a suture cartridge.

4. The method according to claim 1, further comprising securing the retainer cartridge to a surgical instrument.

5. The method according to claim 1, wherein each needle is driven into its respective retainer in a plurality of rows.

6. The method according to claim 1, wherein each needle is driven into its respective retainer and engages the suture, and wherein the suture, the needles, and the retainers define at least one row.

7. The method according to claim 1, wherein the needles are driven so that each retainer is engaged with two of the needles.

8. The method according to claim 1, further comprising cutting the tissue.

9. The method according to claim 1, wherein the needles are driven into holes defined in the retainers.

10. The method according to claim 1, wherein driving each of the needles includes camming the needles from the needle cartridge.

11. The method according to claim 1, wherein the tortured path section inhibits the length of the suture from moving in the second direction by pinching a portion of the length of the suture.

12. The method according to claim 1, further comprising withdrawing each needle from its respective retainer to separate the suture from the needle.

13. A method of securing tissue, comprising:
   clamping tissue between a retainer cartridge and a needle cartridge;
   driving a first needle out of the needle cartridge and through a first retainer of the retainer cartridge to draw a first length of a suture through the first retainer, the first length of the suture retained in the first retainer by a tortured configuration defined by the first retainer which prevents any of the first length of the suture drawn through the tortured configuration of the first retainer from withdrawing from the first retainer through the tortured configuration; and
   separating the retainer cartridge from the needle cartridge to withdraw the first needle from the first retainer and to separate the first retainer from the retainer cartridge.

14. The method according to claim 13, further comprising:
   driving a second needle out of the needle cartridge and through a second retainer of the retainer cartridge to draw a second length of the suture through the second retainer, the second length of the suture being retained in the second retainer by a tortured configuration defined by the second retainer which prevents any of the second length of the suture drawn through the tortured configuration of the second retainer from withdrawing from the second retainer through the tortured configuration; and
   wherein separating the retainer cartridge from the needle cartridge includes withdrawing the second needle from the second retainer and separating the second retainer from the retainer cartridge.

15. The method according to claim 13, further comprising repeating driving and withdrawing for each of a plurality of needles such that each needle of the plurality of needles draws a length of the suture through a respective retainer of a plurality of retainers such that the length of the suture is retained in a tortured configuration defined by the respective retainer of the plurality of retainers which prevents any of the suture drawn through the tortured configuration from withdrawing from the respective retainer of the plurality of retainers and separates each of the respective retainers from the retainer cartridge.

16. A method of securing tissue, comprising:
   clamping tissue between a retainer cartridge and a needle cartridge;
   driving a first needle out of the needle cartridge and through a first retainer of the retainer cartridge to draw a first length of a suture through the clamped tissue, a second needle out of the needle cartridge and through a second retainer of the retainer cartridge to draw a second length of the suture through the clamped tissue, and a third needle out of the needle cartridge and through a third retainer of the retainer cartridge to draw a third length of the suture through the clamped tissue, each of the first, second, and third lengths of the suture retained in the first, second, and third retainers, respectively by a tortured configuration defined by each of the first, second, and third retainers which prevents any of the first, second, and third lengths of the suture drawn through the tortured configuration from withdrawing from the respective retainer, the first, second, and third retainers coupled to the retainer cartridge in an initial configuration of the retainer cartridge; and
withdrawing the first, second, and third needles from the first, second, and third retainers, respectively.

* * * * *